United States Patent [19]
Cook et al.

[11] Patent Number: 5,817,300
[45] Date of Patent: Oct. 6, 1998

[54] ODOR REDUCING COMPOSITIONS

[75] Inventors: John B. Cook, Phoenixville, Pa.; Louis L. Wood, Rockville; Gary J. Calton, Elkridge, both of Md.

[73] Assignee: Calwood Chemical Industries, Inc., Elkridge, Md.

[21] Appl. No.: 867,213

[22] Filed: Jun. 2, 1997

[51] Int. Cl.$^6$ .............................. A61K 7/34; A61L 9/04; A61L 11/00; A61F 5/44

[52] U.S. Cl. ...................... 424/66; 424/76.3; 424/76.5; 424/76.6; 424/76.8; 604/359; 604/360; 604/365

[58] Field of Search .................... 424/66, 76.5, 76.6, 424/76.8, 617, DIG. 5, 76.3; 604/359, 360, 365, 358

[56] References Cited

U.S. PATENT DOCUMENTS

| | | |
|---|---|---|
| 4,719,030 | 1/1988 | Williams et al. . |
| 4,988,505 | 1/1991 | Watanabe et al. . |
| 5,013,335 | 5/1991 | Marcus . |
| 5,135,664 | 8/1992 | Burnham . |
| 5,135,743 | 8/1992 | Stanislowski et al. . |
| 5,211,870 | 5/1993 | Gilbert et al. . |
| 5,306,487 | 4/1994 | Karapasha et al. . |
| 5,587,157 | 12/1996 | Cox et al. ............................. 424/76.5 |

OTHER PUBLICATIONS

Chemical Abstract vol. 110, No. 194 559, Sato et al, Odor-absorbing Polyester Fibers, 1987.

*Primary Examiner*—John Kight
*Assistant Examiner*—Raymond Covington
*Attorney, Agent, or Firm*—William S. Ramsey

[57] ABSTRACT

Zirconium compounds reduce odors. Zirconium hydroxide and sulfated zirconium are especially efficient at reducing the odors of primary, secondary and tertiary amines or ammonia. Zirconium hydroxide and/or sulfated zirconium may be incorporated in pads which are the recipients of odoriferous waste materials, dispersed in holding tanks or lagoons or dispersed over human and animal wastes.

15 Claims, No Drawings

ODOR REDUCING COMPOSITIONS

FIELD OF THE INVENTION

This invention relates to the use of zirconia compounds for the reduction of odors.

DESCRIPTION OF RELATED ART

Odor control has been a significant problem for which there are very few solutions. Amines and ammonia are especially troublesome as odors. Their volatility makes them quite noticeable when even small amounts are released. U.S. Pat. No. 5,013,335 discloses the use of zeolites for control of ammonia odor. U.S. Pat. No. 5,211,870 discloses the use of zeolites in bar soaps to reduce odor. U. S. Pat. No. 4,988,505 discloses the use of antimony pentoxide to reduce the odor of amine containing gases. U.S. Pat. No. 5,135,664 discloses the use of pH to control the emissions of volatile amines in sludge. U.S. Pat. No. 5,135,743 discloses the use of boric acid and pine oil to reduce the odor of animal litter. U.S. Pat. 5,306,487 discloses the use of gelling compositions in which the odor controlling agents, zeolites and carbon, are incorporated by means of a binder. U.S. Pat. No. 5,211,870 discloses the use of zeolites within a cleansing bar for control of odor. U.S. Pat. No. 4,719,030 discloses a translucent soap bar containing sodium aluminosilicate. Co-pending application 08/635,502 discloses the use of imides for odor control

SUMMARY OF THE INVENTION

We have found that zirconium compounds, especially zirconium hydroxide and sulfated zirconium, reduce noxious odors, especially those due to basic compounds such as amines. The zirconium compounds which function effectively in this odor reduction are zirconium hydroxide, having a molecular formula of $Zr(OH)_4$ and sulfated zirconium, having a molecular formula of $ZrO_2 \cdot yH_2O \cdot xSO_4$, where x and y represent integers of variable and/or unknown numbers. Reference to the removal of noxious odors by zirconium compounds may be thought of as scavenging odors from the surrounding atmosphere by removal of a quantity of the amine, ammonia or of acids by reaction or possibly by absorption or adsorption.

The use of the zirconium hydroxide and/or sulfated zirconium for removal of odor is envisioned to be valuable for incorporation into personal care products such as diapers, both adult and infant, incontinent pads, surgical sponges and dressings, surgical pads, catamenial devices such as sanitary napkins, shields, liners, tampons, meat trays especially for fish, bath mats and the like. Such pads can be composed of polyurethane, cellulose, alginate, gelatin, carrageenan, polystyrene, polyolefin or mixtures thereof and may include additional layers to facilitate use in their respective field. Zirconium hydroxide and/or sulfated zirconium can also be incorporated in holding facilities, including foul smelling lagoons, such as those containing animal wastes, or tanks, especially those used for holding human, pig, cattle or other farm wastes, and more especially when the zirconium hydroxide and/or sulfated zirconium are incorporated in films to prevent escape of odors. They can also be used to reduce the odor from sulfite liquor waste ponds or other similar industrial waste treatment facilities. Such reduction can be achieved by mixing the zirconium hydroxide and/or sulfated zirconium with the waste or by depositing the zirconium hydroxide and/or sulfated zirconium on an inert or biodegradable object and mixing the object or allowing the object to come into contact with the waste at the surface, in the body of the waste or on the bottom of the lagoon, holding tank or pond. Thus, the zirconium hydroxide and/or sulfated zirconium can be dispersed on particles, such as clay or other absorbent inorganic or organic materials, for use in controlling odors in animal litter. The zirconium hydroxide and/or sulfated zirconium can be dispersed by spraying or spreading as powders, or held by means of binders. Alternatively, the zirconium hydroxide and/or sulfated zirconium may be retained on a floating object to allow the zirconium hydroxide and/or sulfated zirconium to remain on the surface of a holding facility, such as a pond, lagoon or tank. The floating object may be a film or a particle, especially a biodegradable particle, such as those obtained from corn, rice, wheat, cellulose, soy or rye or fractions thereof or blends thereof, especially when puffed. For sewage in holding facilities, such as portable toilets whether stationary, in planes, trains, boats or mobile homes or the like, floating particles would are advantageous for control of odor as the maximum effect would be available at the liquid-gaseous interface through which the volatiles must pass. Dispersion of the aqueous slurries, or aqueous solutions or solids on liquid or solid animal wastes including fowl, pig and cattle pens to reduce ammonia and amine levels can prevent harmful effects of the ammonia/amines to the animals as well as reducing the release of objectionable odors to the environment. Solutions or powders may be dispersed on articles or places where animal or human wastes have been deposited, especially urine. Thus, zirconium hydroxide and/or sulfated zirconium can be incorporated into cleaners for rugs or clothing, for aqueous solutions for dipping articles, such as clothes, furnishings, shoes, and other items which might easily come into contact with human or animal urine, for removal of odors. Sprays to remove odors from the air can also be prepared. Additionally, the zirconium hydroxide and/or sulfated zirconium may be combined with release agents, such as enzymes or hydrolytic bases or acids, to transform the odoriferous chemical to one which will readily deodorize by the addition of an zirconium hydroxide and/or sulfated zirconium. Enzymes such as ureases or other enzymes which produce an amine or ammonia as a byproduct may be used.

Zirconium hydroxide and/or sulfated zirconium are especially valuable in the reduction of odor as the materials can be placed behind polymeric barriers or woven or non-woven fabrics through which the odor such as that of an organic acid, an amine or ammonia for example, may pass, either in particle form or adsorbed in another material such as cellulose or incorporated in another material such as acrylate polymer, thus preventing contact with the source of the odor. An example of this use is in the production of a diaper containing a plastic barrier or woven or non-woven fabrics through which urine and the amines, ammonia and organic acids present and responsible for much of the odor can pass to the cellulose floc and optionally the polyacrylate superabsorbent placed there for absorbency, either of which or both may contain the zirconium hydroxide and/or sulfated zirconium or upon which the zirconium hydroxide and/or sulfated zirconium may reside. This in turn not only reduces the odor but also reduces irritation of the skin of the subject wearing the diaper.

Likewise, the zirconium hydroxide and sulfated zirconium of the present invention could be incorporated in catamenial devices to reduce the odors thereof. Bandages are yet another area where the zirconium hydroxide and/or sulfated zirconium could be used to reduce odor. Pads made containing these materials, deposited on the surface or contained within a reservoir, could be used to prevent odor caused by leakage in persons where bladder sphincter control is compromised. Such pads could also be placed in the vents of holding vessels for diapers, sewage or other containers of amines or ammonia to prevent odor escape.

It has been found advantageous in many of the above mentioned applications that the zirconium compounds be dispersed in combination with one or more water soluble polymers that help bind the zirconium compounds together or onto surfaces, thus suppressing any dusting of the compounds. Suitable water soluble polymers are hydroxypropyl ellulose, hydroxethyl cellulose, carboxymethyl cellulose, hydropropylcarboxymethyl cellulose, hydroxyethylcarboxymethyl cellulose, poly(vinyl alcohol), poly(acrylic acid) or its salts, poly(acrylamide), poly(methacrylic acid) or its salts, polyoxyethylene, polyoxypropylene, water soluble starch, guar gum, agar, carrageenan, gelatin or the like, either singularly or in combination.

Although it is well known that zirconium hydroxide and/or sulfated zirconium react readily with amines or amrnonia, it has not been appreciated that zirconium hydroxide and/or sulfated zirconium could be used to control odor. The reduction of odor wherein the amine or ammonia and the zirconium hydroxide and/or sulfated zirconium are in contact through a solvent in which one or both is soluble is effective. Contact through an aqueous solution or interface is especially effective.

The object of this invention is to provide a method for the reduction of odors, especially those due to ammonia or amines. Another object of this invention is to provide a method for the removal of ammonia or amines from aqueous, organic or gaseous streams. Yet another object of this invention is to provide a method of treating animal waste products to reduce or eliminate the ammonia or amine containing components by reaction with a suitable zirconium hydroxide and/or sulfated zirconium. Still another object of this invention is to provide a method of treating personal care products such as diapers, both adult and infant, incontinent pads, surgical sponges and dressings, surgical pads, catamenial devices such as sanitary napkins, shields, liners, tampons, meat trays especially for fish, bath mats and the like, to reduce the odor of the waste products deposited there in normal usage of the product. A further object of this invention is the use of an zirconium hydroxide and/or sulfated zirconium for reduction of odor in animal litter. Yet another object of the invention is the reduction of odor in foul smelling lagoons or holding tanks, such as those containing human or animal wastes, especially those used for holding pig, cattle or other farm wastes, or from sulfite liquor waste ponds or other industrial waste treatment facilities where odor control is important. Still another object of the invention is the method of treating the above odors wherein the zirconium hydroxide and/or sulfated zirconium are incorporated in films, gels or solutions to reduce odors.

DETAILED DESCRIPTION OF THE EMBODIMENTS.

EXAMPLE 1.

Dispersion of zirconia on cellulose fiber.

A 2% solution of hydroxypropyl cellulose in water was prepared and the materials were added as indicated. The slurry of test material in hydroxypropyl cellulose were spread over the surface of a paper towel and allowed to dry for 6 hrs at 65° C. to give a coating. The white coated paper towel was flexible. Each of the materials was tested for odor by enclosing a segment of the treated paper towel containing a known amount of test compound in a filter paper and placing this in a 500 mL screw capped jar along with a 6 cm diameter disk of filter paper containing the indicated quantity of odiferous material. The jars were sealed and allowed to stand at 25° C. for the period of time indicated in the table below. The jars were opened periodically as indicated in the table, assessed for odor and rated on a scale of 0 =no odor to 10 =starting odor. The following results were obtained as indicated for the odorant given in the table heading. The amine/ammonia odorant consisted of a aqueous solution containing 10% ammonia, 10% methyl amine, 10% diethyl amine and 10% n-butyl amine.

TABLE 1 triethyl amine (0.1 g)

| Test Material | conc. applied | total applied (g) | Time (hrs) | | | |
|---|---|---|---|---|---|---|
| | | | 2 | 4 | 6 | 12 |
| sulfated zirconia | 40% | 1 | 1 | 0 | 0 | 0 |
| | 25% | 1 | 1 | 0 | 0 | 0 |
| | | 0.5 | 6 | 5 | 4 | 3 |
| | 6.25% | 0.2 | 10 | 10 | 8 | 5 |
| zirconium hydroxide | 75% | 2 | 1 | 0 | 0 | 0 |
| | 58% | 1 | 1 | 0 | 0 | 0 |
| | | 0.5 | 6 | 4 | 2 | 1 |
| | 22% | 0.2 | 10 | 10 | 10 | 8 |
| zinc oxide | 40% | 2 | 10 | 10 | 10 | 9 |
| zeolite 4A | 40% | 2 | 9 | 8 | 6 | 5 |
| polysuccinimide | | 0.5 | 10 | 10 | 10 | 10 |

Table 1 shows that zirconium hydroxide and sulfated zirconium were superior to zinc oxide and zeolites in removing odors of triethyl amine.

TABLE 2 amine/ammonia mixture (0.5 g)

| Test Material | conc. applied | total applied | Time (hrs) | | | |
|---|---|---|---|---|---|---|
| | | | 2 | 4 | 6 | 12 |
| sulfated zirconium | 40% | 1 | 1 | 0 | 0 | 0 |
| | 25% | 1 | 1 | 1 | 1 | 1 |
| | | 0.5 | 6 | 4 | 2 | 0 |
| | 6.25% | 0.2 | 9 | 6 | 5 | 5 |
| zirconium hydroxide | 75% | 2 | 1 | 0 | 0 | 0 |
| | 58% | 1 | 3 | 2 | 2 | 0 |
| | | 0.5 | 7 | 5 | 3 | 1 |
| | 22% | 0.2 | 9 | 7 | 7 | 7 |
| zinc oxide | 40% | 2 | 10 | 10 | 10 | 10 |
| zeolite 4A | 40% | 2 | 10 | 10 | 10 | 10 |
| polysuccinimide | | 0.5 | 6 | 5 | 4 | 1 |

Table 2 shows that zirconium hydroxide and sulfated zirconium were superior to zinc oxide and zeolites in removing odors of methyl, diethyl, and n-butyl amines and ammonia. It also shows that some zeolites are ineffective in controlling amine/ammonia odors.

TABLE 3 iso-butyric acid (0.1 g)

| Test Material | conc. applied | total applied | Time (hrs) | | | |
|---|---|---|---|---|---|---|
| | | | 2 | 4 | 6 | 12 |
| sulfated zirconium | 40% | 1 | 4 | 2 | 1 | 0 |
| | 25% | 1 | 5 | 2 | 2 | 0 |
| | | 0.5 | 5 | 2 | 2 | 0 |
| | 6.25% | 0.2 | 8 | 8 | 7 | 6 |
| zirconium hydroxide | 75% | 2 | 3 | 1 | 0 | 0 |
| | 58% | 1 | 4 | 2 | 2 | 0 |
| | | 0.5 | 4 | 1 | 1 | 0 |

TABLE 3-continued iso-butyric acid (0.1 g)

| Test Material | conc. applied | total applied | Time (hrs) | | | |
|---|---|---|---|---|---|---|
| | | | 2 | 4 | 6 | 12 |
| zinc oxide | 22% | 0.2 | 8 | 6 | 5 | 3 |
| zeolite 4A | 40% | 2 | 4 | 4 | 3 | 3 |
| polysuccinimide | 40% | 2 | 5 | 4 | 4 | 4 |
| | | 0.5 | 10 | 10 | 10 | 10 |

Table 3 shows that zirconium hydroxide and sulfated zirconium were superior to zinc oxide and zeolites in removing odors of iso-butyric acid.

EXAMPLE 2.

Evaluation of various deodorants in the presence of 1 % sodium chloride in water.

Preparations of 4×6 inch sheets, prepared as in Example 1, were made to contain 1 g of active material. To each sheet was then added 3 g of aqueous 1% NaCl solution. Each of the materials was tested for odor as in Example 1. The following results were obtained as indicated for the odorant given.

TABLE 4 triethyl amine (0.1 g)

| Test Material | Time (hrs) | | | |
|---|---|---|---|---|
| | 2 | 4 | 6 | 12 |
| sulfated zirconium | 0 | 0 | 0 | 0 |
| zirconium hydroxide, | 0 | 0 | 0 | 0 |
| aluminum hydroxide | 0 | 0 | 0 | 0 |
| activated carbon | 0 | 0 | 0 | 0 |
| polysuccinimide | 0 | 0 | 0 | 0 |
| blank | 8 | 7 | 7 | 5 |

Table 4 shows the materials tested were effective deodorants for tertiary amines.

TABLE 5 amine/ammonia mixture (0.5 g)

| Test Material | Time (hrs) | | | |
|---|---|---|---|---|
| | 2 | 4 | 6 | 12 |
| sulfated zirconium | 2 | 1 | 1 | 0 |
| zirconium hydroxide | 7 | 6 | 5 | 3 |
| aluminum hydroxide | 1 | 0 | 0 | 0 |
| activated carbon | 0 | 0 | 0 | 0 |
| polysuccinimide | 0 | 0 | 0 | 0 |
| blank | 8 | 6 | 6 | 4 |

Table 5 shows the materials tested were effective deodorants for ammonia, primary and secondary amines.

TABLE 6 iso-butyric acid (0.1 g)

| Test Material | Time (hrs) | | | |
|---|---|---|---|---|
| | 2 | 4 | 6 | 12 |
| sulfated zirconium | 1 | 0 | 0 | 0 |
| zirconium hydroxide | 0 | 0 | 0 | 0 |
| aluminum hydroxide | 3 | 0 | 0 | 0 |
| activated carbon | 3 | 3 | 3 | 1 |
| polysuccinimide | 5 | 5 | 5 | 4 |
| blank | 5 | 5 | 5 | 4 |

Table 6 shows the materials with the exception of polysuccinimide removed the odor of iso-butyric acid.

EXAMPLE 3.

Evaluation of various deodorants in an adult incontinance product.

Preparations of 4×6 inch sections of Depends™, an adult diaper made by Kimberly Clark, were opened in the center layer of absorbent and 1 g portions of particles were placed within the absorbent sheet. To each sheet was then added 3 g of aqueous 1% NaCl solution. Each of the materials was tested for odor as in Example 1. The following results were obtained as indicated for the odorant given.

TABLE 7 triethyl amine (0.1 g)

| Test Material | Time (hrs) | | | |
|---|---|---|---|---|
| | 2 | 4 | 6 | 12 |
| sulfated zirconium | 0 | 0 | 0 | 0 |
| zirconium hydroxide | 0 | 0 | 0 | 0 |
| aluminum hydroxide | 0 | 0 | 0 | 0 |
| activated carbon | 0 | 0 | 0 | 0 |
| polysuccinimide | 0 | 0 | 0 | 0 |
| blank | 8 | 7 | 7 | 5 |

Table 7 shows the materials tested were effective deodorants for tertiary amines in diapers.

TABLE 8 amine/ammonia mixutre (0.5 g)

| Test Material | Time (hrs) | | | |
|---|---|---|---|---|
| | 2 | 4 | 6 | 12 |
| sulfated zirconium | 2 | 1 | 1 | 0 |
| zirconium hydroxide | 7 | 6 | 5 | 3 |
| aluminum hydroxide | 1 | 0 | 0 | 0 |
| activated carbon | 0 | 0 | 0 | 0 |
| polysuccinimide | 0 | 0 | 0 | 0 |
| blank | 8 | 6 | 6 | 4 |

Table 8 shows that the materials tested were effective deodorants for ammonia, primary amines and secondary amines when incorporated in diapers.

TABLE 9

| | iso-butyric acid (0.1 g) | | | |
| --- | --- | --- | --- | --- |
| | Time (hrs) | | | |
| Test Material | 2 | 4 | 6 | 12 |
| sulfated zirconium | 1 | 0 | 0 | 0 |
| zirconium hydroxide | 0 | 0 | 0 | 0 |
| aluminum hydroxide | 3 | 0 | 0 | 0 |
| activated carbon | 3 | 3 | 3 | 1 |
| polysuccinimide | 5 | 5 | 5 | 4 |
| blank | 5 | 5 | 5 | 4 |

Table 9 shows the materials with the exception of polysuccinimide removed the odor of iso-butyric acid when incorporated in diapers.

It will be apparent to those skilled in the art that the examples and embodiments described herein are by way of illustration and not of limitation, and that other examples may be utilized without departing from the spirit and scope of the present invention, as set forth in the appended claims.

We claim:

1. A method of removing odor comprising contacting said odor with a zirconium compound selected from the group of zirconium compounds consisting of zirconium hydroxide and sulfated zirconium.

2. The method of claim 1 wherein said compound is zirconium hydroxide.

3. The method of claim 1 wherein said compound is sulfated zirconium.

4. The method of claim 1 wherein said odor results from ammonia or an amine.

5. The method of claim 1 wherein said odor results from an organic acid.

6. The method of claim 1 wherein said compound is incorporated in a pad.

7. The method of claim 6 wherein said pad is a pad selected from the group of pads consisting of diapers, incontinent pads, surgical sponges, surgical dressings, catamenial devices, meat trays and bath mats.

8. The method of claim 6 wherein said compound is incorporated by means of deposition on said pad.

9. The method of claim 6 wherein said pad is a bandage.

10. The method of claim 6 wherein said pad is a diaper.

11. The method of claim 6 wherein said catamenial device is a sanitary napkin, a shield, a liner or a tampon.

12. A diaper comprising an odor absorbing quantity of a zirconium compound selected from the group of zirconium compounds consisting of zirconium hydroxide and sulfated zirconium, a superabsorbent gel and an absorbent pad.

13. A catamenial device comprising an odor absorbing quantity of a zirconium compound selected from the group of zirconium compounds consisting of zirconium hydroxide and sulfated zirconium and an absorbent pad.

14. The method of claim 1 further comprising the step: binding said zirconium compound together with or onto a surface using a water soluble polymer.

15. The method of claim 14 wherein said water soluble polymer is chosen from the group consisting of hydroxypropyl cellulose, hydroxethyl cellulose, carboxymethyl cellulose, hydropropylcarboxymethyl cellulose, hydroxyethylcarboxymethyl cellulose, poly(vinyl alcohol), poly(acrylic acid) or its salts, poly(acrylamide), poly(methacrylic acid) or its salts, polyoxyethylene, polyoxypropylene, water soluble starch, guar gum, agar, carrageenan and gelatin, either singularly or in combination.

* * * * *